US00PP23924P2

(12) United States Plant Patent
Smith

(10) Patent No.: US PP23,924 P2
(45) Date of Patent: Sep. 24, 2013

(54) *CHRYSANTHEMUM* PLANT NAMED 'CIFZ0031'

(50) Latin Name: *Chrysanthemum×morifolium*
Varietal Denomination: CIFZ0031

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 87 days.

(21) Appl. No.: 13/385,243

(22) Filed: Feb. 9, 2012

(51) Int. Cl.
*A01H 5/00* (2006.01)

(52) U.S. Cl.
USPC ..... Plt./290; Plt./284; Plt./286; Plt./287

(58) Field of Classification Search
USPC ..... Plt./284, 286, 287, 290
See application file for complete search history.

*Primary Examiner* — Susan McCormick Ewoldt
(74) *Attorney, Agent, or Firm* — Joshua L. Price

(57) ABSTRACT

A new *Chrysanthemum* plant named 'CIFZ0031' particularly distinguished by the small orange decorative inflorescences, medium yellow-green foliage color, compact and rounded plant habit, with a natural season flowering response of late September or early October.

1 Drawing Sheet

Latin name of the genus and species of the plant claimed: *Chrysanthemum×morifolium.*

Varietal denomination: 'CIFZ0031'.

BACKGROUND OF THE NEW PLANT

The present invention comprises a new *Chrysanthemum*, botanically known as *Chrysanthemum×morifolium*, and hereinafter referred to by the variety name 'CIFZ0031'.

'CIFZ0031' is a product of a planned breeding program. The new cultivar has small orange decorative inflorescences, medium yellow-green foliage color, compact and rounded plant habit, with a natural season flowering response of late September or early October.

'CIFZ0031' originated from a hybridization made in December 2006 in a controlled breeding environment in a greenhouse in Amanecer, Columbia. The female parent was the proprietary plant designated 'Yoashley', U.S. Plant Pat. No. 18,916, with lighter shade of orange inflorescences, little larger plant size and a black cloth flowering response that is half a week slower than 'CIFZ0031'.

The male parent of 'CIFZ0031' was the unpatented, proprietary plant designated as '04-M173' with larger, pink/lavender inflorescence color, more disc florets, a little smaller plant size with a natural season flowering response that is two weeks faster than that of 'CIFZ0031'. The resultant seed was sown and grown outdoors in June 2007 in Alva, Fla.

'CIFZ0031' was selected as one flowering plant within the progeny of the stated cross in November 2007 in Alva, Fla.

The first act of asexual reproduction of 'CIFZ0031' was accomplished when vegetative cuttings were propagated from the initial selection in January 2008 in a greenhouse in Alva, Fla.

BRIEF SUMMARY OF INVENTION

Horticultural examination of plants grown from cuttings of the plant initiated in January 2008, and continuing thereafter, has demonstrated that the combination of characteristics as herein disclosed for 'CIFZ0031' are firmly fixed and are retained through successive generations of asexual reproduction.

'CIFZ0031' has not been observed under all possible environmental conditions. The phenotype may vary significantly with variations in environment such as temperature, light intensity, and day length.

A Plant Breeder's Right for this cultivar was applied for in Canada on Feb. 24, 2011, No. 11-7188. 'CIFZ0031' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

Figure 1:
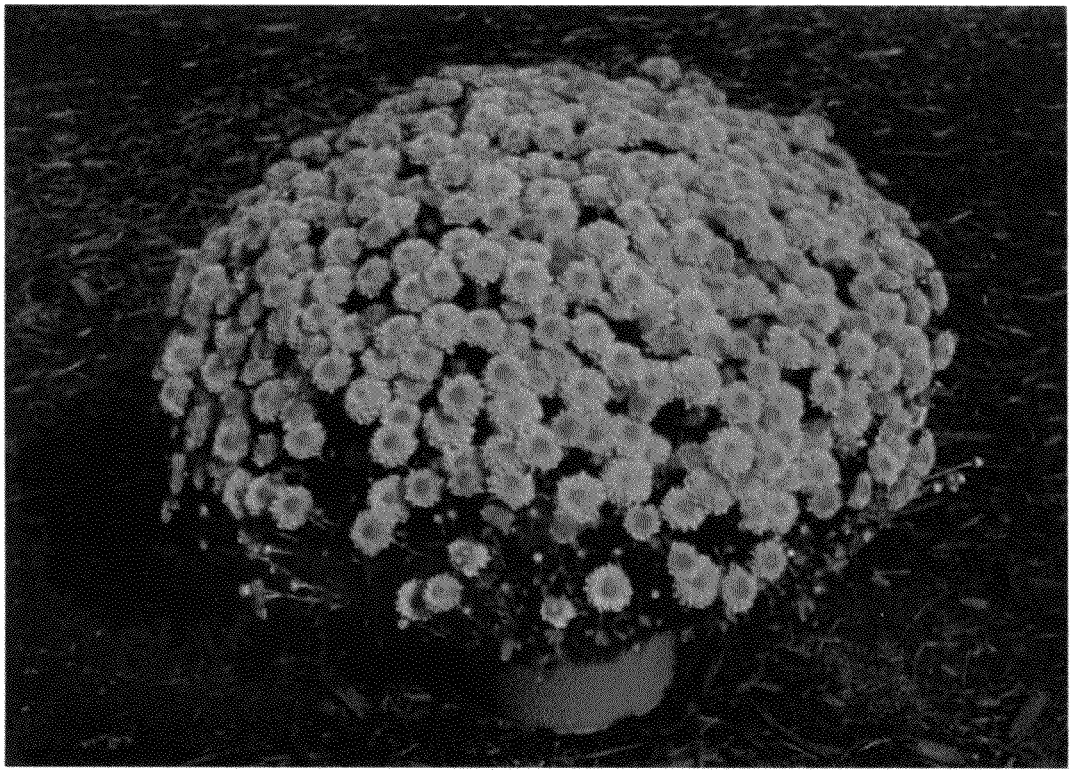
Figure 2:
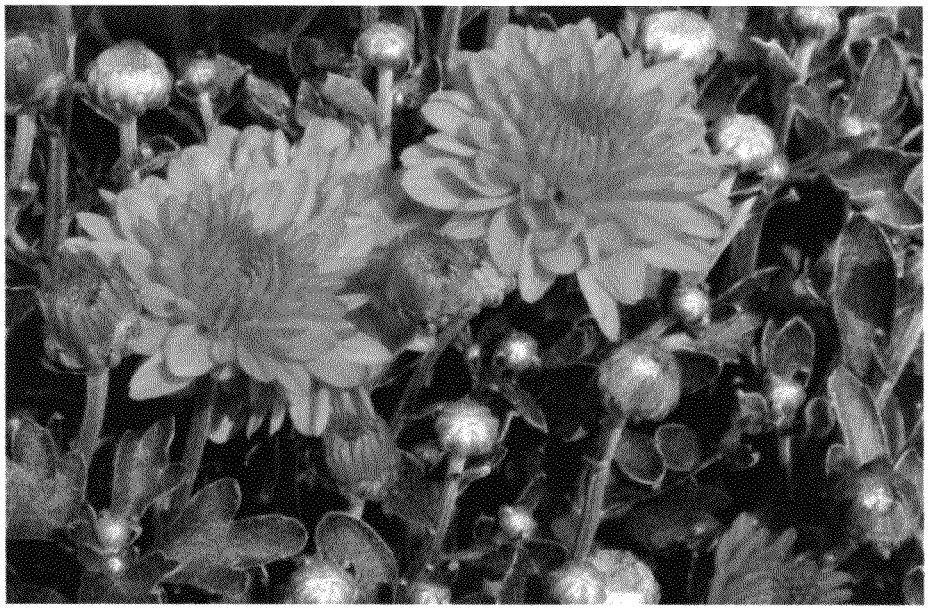

The accompanying photographic drawings show typical flower and foliage characteristics of 'CIFZ0031' with colors being as true as possible with an illustration of this type. The photographic drawings show in FIG. 1 a flowering potted plant of the new variety and in FIG. 2 a close-up of the inflorescences.

The close-up photograph was taken outdoors in Gilroy, Calif. in August 2011. These plants were grown outdoors in gallon pots and were approximately 9 weeks of age. The aforementioned photograph of the whole plant was taken in mid-October 2010 in Monroeville, N.J. and plants were about 15-16 weeks old, grown outdoors.

DETAILED BOTANICAL DESCRIPTION

The plant descriptions and measurements were collected outdoors in Gilroy, Calif. in August 2011. These plants were grown outdoors in gallon pots and were approximately 9 weeks of age.

Color references are made to The Royal Horticultural Society Colour Chart (R.H.S.) 2001.

TABLE 1

DIFFERENCES BETWEEN THE NEW VARIETY 'CIFZ0031' AND A MOST SIMILAR VARIETY

| | 'CIFZ0031' | 'Yoolivia' (U.S. Plant Pat. No. 13,806) |
|---|---|---|
| Ray floret color: | Darker orange overlay | Lighter orange overlay |
| Disc floret quantity: | Much fewer | Many more |
| Black cloth flowering response: | 2 weeks earlier in heat | 2 weeks later in heat |

Plant:

*Form, growth and habit.*—Herbaceous garden-type, stems upright and outwardly spreading, freely branching, strong and moderately vigorous growth habit.

*Plant height.*—20.0 cm.

*Plant height* (*inflorescence included*).—23.0-25.0 cm.

*Plant width.*—34.0-37.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A but a little more grey.

*Lower surface.*—Closest to RHS 137B.

*Mature, leaf color, upper surface.*—Closest to RHS 147A but a little more grey.

*Lower surface.*—Closest to RHS 137B.

*Length.*—3.7-5.0 cm.

*Width.*—3.3-3.7 cm.

*Shape.*—Ovate.

*Base shape.*—Attenuate.

*Apex shape.*—Mucronulate.

*Margin.*—Palmately lobed; irregularly incised; serrate.

*Texture, upper surface.*—Bifid T-shaped hairs.

*Lower surface.*—Bifid T-shaped hairs.

*Color of veins, upper surface.*—RHS 144B.

*Color of veins, lower surface.*—RHS 147C.

*Petiole color.*—Closest to RHS 147C but a little more yellow.

*Length.*—1.9-2.1 cm.

*Diameter.*—0.2 cm.

*Texture.*—Bifid T-shaped hairs.

Stem:

*Quantity of main branches per plant.*—7-10.

*Color of stem.*—RHS 138A but appears lighter because of hairs.

*Length of stem.*—10.0-12.0 cm.

*Diameter.*—0.4.

*Length of internodes.*—0.5-0.7 cm.

*Texture.*—Bifid T-shaped hairs.

*Color of peduncle.*—RHS 138A but appears lighter due to hairs.

*Length of peduncle.*—7.5-8.0 cm.

*Peduncle diameter.*—0.25 cm.

*Texture.*—Bifid T-shaped hairs.

Inflorescence:

*Type.*—Compositae, solitary decorative-type inflorescences, borne terminally above foliage, ray florets arranged acropetally on a capitulum.

*Quantity of inflorescences per plant.*—35-40 with 100-130 buds.

*Lastingness of individual blooms on the plant.*—More than 6 weeks from first color sowing.

*Fragrance.*—Slightly spicy.

Bud (just when opening/showing color):

*Color.*—Closest to RHS 185A but a little richer hue.

*Length.*—1.0-1.3 cm.

*Width.*—1.0-1.4 cm.

*Shape.*—Oblate.

Immature inflorescence:

*Diameter.*—3.5-4.2 cm.

*Color of ray florets, upper surface.*—RHS 180B with a spot of RHS 2B basally and RHS 181A at the apex.

*Lower surface.*—RHS 179B with a spot of RHS 2B basally.

Mature inflorescence:

*Diameter.*—5.4-5.6 cm.

*Depth.*—1.4-1.6 cm.

*Total diameter of disc.*—Indistinct at this stage.

*Receptacle height.*—0.3-0.4 cm.

*Receptacle diameter.*—0.5 cm.

Ray florets:

*Average quantity of florets.*—About 200 in several whorls.

*Color of florets, upper surface.*—RHS 4B, heavily overlaid with between RHS 171C and RHS 170A with RHS 172B at the margins and apex.

*Lower surface.*—RHS 163C, overlaid with RHS 172A heavily down the middle, and with RHS 172B at the margins and RHS 2B basally.

*Length.*—1.8-1.9 cm.

*Width.*—0.6-0.7 cm.

*Shape.*—Elliptical.

*Apex shape.*—Obtuse, some emarginate.

*Margin.*—Entire.

*Texture, upper surface.*—Papillose.

*Lower surface.*—Papillose.

Disc florets:

*Average quantity of florets.*—2.

*Color of florets.*—RHS 3B with a hint of RHS 40B at the apex.

*Length.*—0.2-0.3 cm

*Width.*—0.1 cm.

*Shape.*—Tubular, elongated.

*Apex shape.*—Acute, 5 pointed.

Phyllaries:

*Quantity.*—About 25.

*Color, upper surface.*—RHS 137B.

*Lower surface.*—RHS 137A but appears lighter due to hairs.

*Length.*—0.3-0.5 cm.

*Width.*—0.15-0.2 cm.

*Shape.*—Lanceolate.

*Apex shape.*—Acute.

*Base.*—Fused.

*Margins.*—Entire; some papery.

*Texture, upper surface.*—Glabrous.

*Lower surface.*—Bifid T-shaped hairs.

Reproductive organs:

*Pistil.*—1, found on both types of florets.

*Length.*—0.35 cm.

*Style color*.—RHS 1C.
*Style length*.—0.30 cm.
*Stigma color*.—RHS 2A.
*Stigma shape*.—Bi-parted.
*Ovary color*.—RHS 155C and very translucent.
*Ovary length*.—0.05 cm.
*Ovary width*.—0.1 cm.
*Stamens*.—4, found on only on the disc florets.
*Color of filaments*.—RHS 1C.
*Length filaments*.—0.2 cm.
*Anther color*.—RHS 15B.
*Anther length*.—0.05 cm.
*Anther shape*.—Oblong.
*Color of pollen*.—RHS 17B.
*Pollen amount*.—Scarce.

What is claimed is:

1. A new and distinct variety of *Chrysanthemum* plant named 'CIFZ0031' substantially as illustrated and described herein.

* * * * *